United States Patent [19]

Ohno et al.

[11] 4,264,497
[45] Apr. 28, 1981

[54] 1,5-BENZOTHIAZEPINE COMPOUNDS

[75] Inventors: Sachio Ohno; Kihachiro Izumi, both of Aichi; Kiyoshi Mizukoshi, Iwakura; Kazuo Kato; Hajimu Yamamoto, both of Nagoya; Mitsuaki Nagasaka, Aichi; Yoshiki Nakamura; Mikio Hori, both of Gifu, all of Japan

[73] Assignee: Maruko Seiyaku Co., Ltd., Nagoya, Japan

[21] Appl. No.: 12,091

[22] Filed: Feb. 14, 1979

[30] Foreign Application Priority Data

Feb. 14, 1978 [JP] Japan .............................. 53/1580078
Jul. 29, 1978 [JP] Japan ................................ 53/92998

[51] Int. Cl.³ ................. C07D 513/00; C07D 281/10; A61K 31/55
[52] U.S. Cl. .............................. 260/239.3 B; 424/244; 260/330.3
[58] Field of Search ........... 260/243.3, 330.3, 239.3 B; 544/359; 549/59

[56] References Cited

U.S. PATENT DOCUMENTS 3,361,760  1/1968  Krapcho ................................ 549/10
3,519,647  7/1970  Krapcho ................................ 549/10

OTHER PUBLICATIONS

Burger, Medicinal Chemistry (1960), Interscience, London, p. 42.

*Primary Examiner*—Anton H. Sutto
*Assistant Examiner*—D. B. Springer
*Attorney, Agent, or Firm*—Sughrue, Rothwell, Mion, Zinn and Macpeak

[57] ABSTRACT

Cis or trans-1,5-benzothiazepine compounds represented by the formula (I):

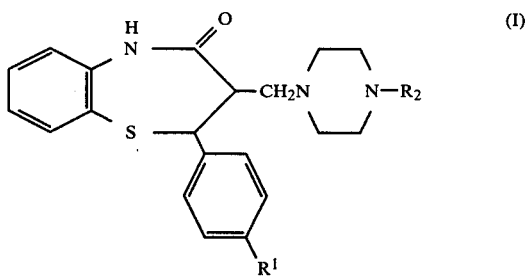

wherein $R_1$ represents a hydrogen atom, a halogen atom, an alkyl group or an alkoxy group and $R_2$ represents a hydrogen atom, an alkyl group or a hydroxyalkyl group and the pharmaceutically acceptable acid addition salts and quaternary ammonium salts thereof which exhibit anticholinergic activity and are useful as anti-ulcer, gastric secretion inhibiting and antispasmodic agents in mammals, and a process for preparing the same.

4 Claims, No Drawings

1,5-BENZOTHIAZEPINE COMPOUNDS

BACKGROUND OF THE INVENTION

1. Field of the Invention

This invention relates to novel cis and trans-1,5-benzothiazepine compounds represented by the formula (I):

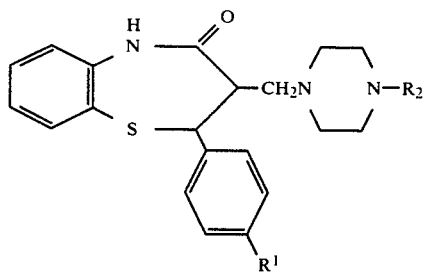

wherein $R_1$ represents a hydrogen atom, a halogen atom, an alkyl group or an alkoxy group and $R_2$ represents a hydrogen atom, an alkyl group or a hydroxyalkyl group and pharmaceutically acceptable acid addition salts and quaternary ammonium salts thereof, and a process for preparing the same.

2. Description of the Prior Art

Hitherto, it is known that cis-(−)-3-acetyloxy-5-(N,N-dimethylamino)ethyl-2-(p-methoxyphenyl)-1,5-benzothiazepin-4(5H)-one hydrochloride is useful as a coronary vasodilator as disclosed in Japanese Patent Publication No. 16988/71, Arzneim.-Forsch. 21(9), 1338–1343 (1971) and Chem. Pharm. Bull., Japan, 21 (1), 92–97 (1973). Also, Journal of Medicinal Chemistry, Vol. 11 (2), P 361, 1968 discloses 5-(N,N-dimethylamino)ethyl-2-phenyl-1,5-benzothiazepin-4(5H)-one hydrochloride as being useful as tranquilizer.

The above known compounds have a chemical structure similar to the compounds of the present invention having the formula (I) but they exhibit completely different pharmacological activity from that of the present invention.

DETAILED DESCRIPTION OF THE INVENTION

The term "halogen" as used herein for $R_1$ means a chlorine atom or a bromine atom, preferably a chlorine atom.

The term "alkyl" as used herein for $R_1$ means a straight or branched chain alkyl group having 1 to 4 carbon atoms, e.g. a methyl, ethyl, n-propyl, isopropyl, n-butyl, sec-butyl or tert-butyl group, preferably a methyl group.

The term "alkoxy" as used herein for $R_1$ means an alkoxy group having 1 to 4 carbon atoms, e.g., a methoxy, ethoxy, propoxy or butoxy group, preferably a methoxy group.

The term "hydroxyalkyl" as used herein for $R_2$ means a hydroxyalkyl group having 2 to 4 carbon atoms, e.g., a hydroxyethyl, hydroxypropyl or hydroxybutyl group, preferably a hydroxyethyl group.

As is apparent to one skilled in the art, the 1,5-benzothiazepin compounds of this invention represented by the formula (I) above contain two asymmetric carbon atoms at the 2- and 3-positions of the 7-membered ring thereof and, therefore, exist cis and trans forms and (+) and (−) forms in each of the steric isomer. It is to be understood that the present invention includes, in the scope thereof, the optically active cis and trans forms as well as cis and trans forms of the compounds of the formula (I), and pharmaceutically acceptable acid addition salts and quaternary ammonium salts of these compounds.

The 1,5-benzothiazepine compounds represented by the formula (I) can be prepared by the following reaction scheme:

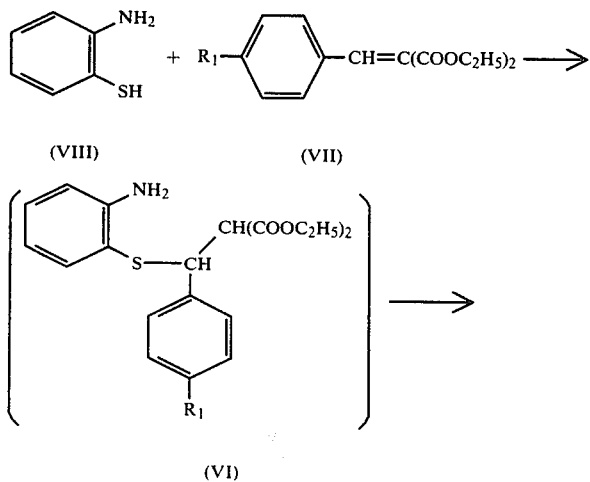

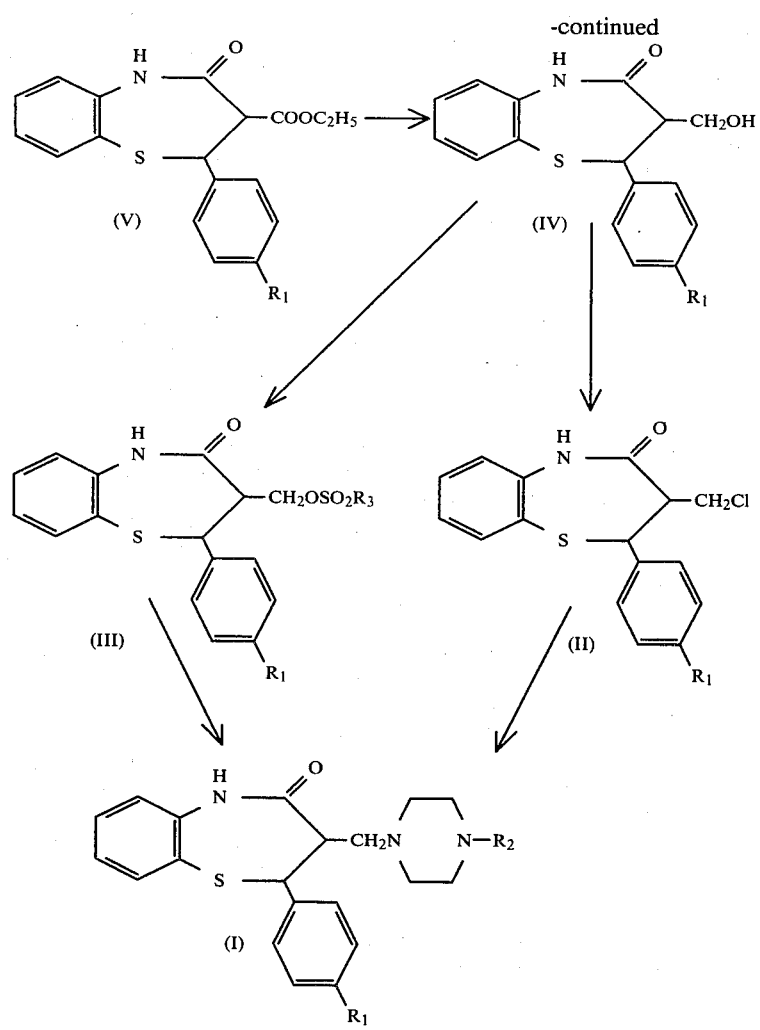

wherein R₁ and R₂ are as defined above and R₃ represents a methyl group or a p-tolyl group.

The process of this invention will be described in greater detail according to the above reaction scheme.

The reaction between o-aminothiophenol (VIII) and an ethyl benzalmalonate (VII) can be carried out using an approximately equimolar amount of these compounds at a temperature of from room temperature (about 15°–30° C.) to about 90° C., preferably 20° to 50° C., for a period of about 3 to 6 hours, generally in the absence of a solvent to obtain an adduct of the formula (VI).

The resulting adduct of the formula (VI) is then heated at a temperature of about 160° to about 180° C. in the presence of a catalyst such as concentrated hydrochloric acid, a tertiary amine hydrochloride, for example, triethylamine hydrochloride, pyridine hydrochloride and the like until no further ethanol formed during cyclization reaction is distilled out from the reaction system to form the corresponding 3-ethoxycarbonyl compound of the formula (V) which is then reduced with a reducing agent, for example, lithium aluminum hydride, calcium borohydride, etc. at a temperature of about 20° C. to about 100° C. in an inert organic solvent such as tetrahydrofuran, dioxane and the like to obtain the corresponding 3-hydroxymethyl compound of the formula (IV).

Alternatively, the reaction between o-aminothiophenol (VIII) and the ethyl benzalmalonate (VII) can be carried out in the presence of the catalyst described above whereby the 3-ethoxycarbonyl compound of the formula (V) can be produced without isolating the adduct of the formula (VI).

The resulting 3-hydroxymethyl compounds of the formula (IV) obtained above are novel compounds and are useful intermediates for the preparation of the desired compounds of the formula (I) via alternative routes through the corresponding 3-chloromethyl compounds of the formula (II) or the corresponding 3-substituted-sulfonyloxymethyl compounds of the formula (III).

The conversion of the 3-hydroxymethyl compound of the formula (IV) into the corresponding 3-chloromethyl compound of the formula (II) can be conducted by reacting the 3-hydroxymethyl compound (IV) with a chlorinating agent such as thionyl chloride, phosphorus oxychloride and the like in an inert organic solvent such as benzene, toluene, chloroform and the like at a temperature of about 60° C. to about 100° C. for a period of about 30 minutes to about 2 hours, using about 1 to about 2 mols of the chlorinating agent per mol of the 3-hydroxymethyl compound (IV). Alternatively, the above convention is preferably conducted in the presence of a catalyst such as a tertiary amine, for example, pyridine, triethylamine and the like whereby the reaction proceeds smoothly.

In an alternative route, the conversion of the 3-hydroxymethyl compound of the formula (IV) into the corresponding 3-substituted-sulfonyloxymethyl compound of the formula (III) can be conducted by reacting the 3-hydroxymethyl compound (IV) with a substituted sulfonyl chloride or bromide in a tertiary amine such as pyridine, triethylamine and the like or a mixture thereof with an inert organic solvent such as benzene, toluene, chloroform and the like at room temperature for a period of from about 1 to about 3 hours, using about 1 to about 2 mols of the substituted sulfonyl chloride or bromide per mol of the 3-hydroxymethyl compound (IV).

The substitution reaction of the compound of the formula (II) or the formula (III) to the desired compound of the formula (I) generally proceeds by reacting the compound (II) or (III) with a piperazine compound in an equimolar amount to a large excess amount which serves as a reactant as well as a reaction solvent at a temperature of about 80° to about 100° C. for about 30 minutes to about 10 hours. A solvent such as dioxane, benzene, toluene and the like can also be used in the reaction. After completion of the reaction, the reaction mixture can be concentrated, if necessary, and poured into water to obtain the desired product of the formula (I) as a mixture of cis and trans forms.

As set forth previously, the compounds of the present invention of the formula (I) have two asymmetric carbon atoms and, therefore, four optically active steric isomers and (±)-cis- and (±)-trans forms exist which have the same chemical structure but are different in the IR absorption spectrum and the melting point. The present inventors studied on the nuclear magnetic resonance spectra of these compounds in order to determine the chemical structure of the compounds and found that one of these isomers showed the coupling constant (J 2,3) of about 6Hz, whereas the other isomer showed the coupling constant (J 2,3) of about 12Hz, which correspond to the cis and trans forms, respectively.

As a result of further studies on the pharmaceutical activities of the optically active compounds of the formula (I), it was found that the compound in (−) form generally exhibits higher anticholinergic and anti-ulcer activities in comparison with the corresponding racemate. For example, in (±)-cis-2,3-dihydro-3-[(4-methylpiperazinyl)methyl]-2-phenyl-1,5-benzothiazepin-4(5H)-one which has been found to have potent gastric secretion inhibitory activity and anti-ulcer activity in comparison with known anticholinergic agents, the (−) form exhibited an anticholinergic activity and anti-ulcer activity of 2 and 4 times the activities of the corresponding racemate, respectively. In addition, the (−) form exhibited a lower desalivation activity as a side-effect to a degree of about ½ and a lower acute toxicity to a degree of ⅔ by oral administration and 2/5 by intravenous administration, in comparison with the corresponding racemate [(±)-cis form] as shown below.

| | Racemic Mixture | (−) Form |
|---|---|---|
| Anticholinergic Activity | 1 | 2 |
| Anti-ulcer Activity (Stress) | 1 | 4 |
| Desalivation Activity | 1 | 0.6 |
| Acute Toxicity (LD$_{50}$ mg/kg) | | |
| Oral in Mice | 650 | 870 |
| Intravenous in Mice | 65 | 160 |

The optical resolution of the racemate of the compounds (I) can be achieved by a conventional procedure, for example, using an optically active acid as resolution agent such as (+) or (−) tartaric acid or a derivative thereof, e.g., (+) or (−) diacetyltartaric acid, (+) or (−) monomethyl tartarate, (+)-camphorsulfonic acid, etc. which are well known in the art.

In a typical procedure for the optical resolution, a racemate of the compound of the formula (I) is reacted with an optically active acid as described above in an equimolar amount in a solvent and the resulting crystalline two optically acitive acid salts are separated by taking advantage of their different solubility. Any types of solvents can be used in the above reaction as long as these solvents have remarkable difference in the solubility between the above salts, but methanol, ethanol or a mixture thereof (e.g., 50:50 by volume) is preferably used.

Each of the optically active salts thus separated is then dissolved in water and the aqueous solution is rendered neutral with an alkali such as sodium carbonate, potassium carbonate and the like to obtain the corresponding free compound in the form of either (+) or (−).

The pharmaceutically acceptable acid addition salts and quaternary ammonium salts of the resulting (+) or (−) compound can be easily obtained by the reaction of the compound with a non-toxic pharmaceutically acceptable inorganic or organic acid such as hydrochloric acid, hydrobromic acid, sulfuric acid, oxalic acid, fumaric acid, maleic acid, succinic acid, citric acid, malic acid and the like or by the reaction with an alkyl halide such as methyl bromide, butyl bromide and the like, in a usual manner as well known in the art.

The acute toxicity and the anticholinergic activity of the typical compound of this invention having the formula (I) in comparison with commercially available typical compounds having a similar activity are set forth below.

Test Compounds
A: Cis-2,3-dihydro-3-[4-methylpiperazinyl)methyl]-2-phenyl-1,5-benzothiazepin-4(5H)-one . 2HCl . H$_2$O (prepared in Example 1 of this invention)
B: Glycopyrrolate (Merck Index, 8th Ed.) (anti-peptic ulcer agent having an excellent activity which has recently been commercially available)
C: Atropin Sulfate (a well-known anti-cholinergic agent)

LD$_{50}$ (in mice)

| Compounds | Oral (mg/kg) | Intravenous (mg/kg) |
|---|---|---|
| A | 650 | 65 |
| B | 860 | 20 |
| C | 500 | 90 |

Anti-ulcer Activity

| Type of Ulcer Induced | Animal (Number) | Administration Route* | Dose (mg/kg) | % Inhibitory A | B | C |
|---|---|---|---|---|---|---|
| Stress | Mice (6) | p.o. | 5 | 91.6 | 81.9 | 82.3 |
| Aspirin | Rats (5) | s.c. | 5 | 100.0 | 100.0 | 79.3 |
| Indomethacin | Rats (6) | p.o. | A:5 B:20 | 99.0 | 88.6 | — |
| Aspirin-Stress Pylorus | Mice (6) | s.c. | 5 | 51.8 | 47.6 | 48.0 |

-continued

| | | | | | | |
|---|---|---|---|---|---|---|
| Ligature | Rats (5) | s.c. | 20 | 100.0 | 100.0 | 13.0 |

*p.o.:Oral Administration
s.c.:Subcutaneous Administration

GASTRIC SECRETION INHIBITORY ACTIVITY

The gastric secretion inhibitory activity of the test compounds were observed simultaneously in the above anti-ulcer activity test using aspirin and the results are as follows:

| Test Compounds | % Inhibitory |
|---|---|
| A | 90 |
| B | 90 |
| C | 70 |

The corediastasis which is considered as one of serious side effects frequently observed in administering anticholinergic agents was found to be 0.31 mg/kg (Compound A), 0.037 mg/kg (Compound B) and 0.076 mg/kg (Compound C) in terms of $ED_{20}$ by intraperitoneal administration.

As is apparent from the above pharmacological data, Compound A of the present invention shows approximately the same degree of acute toxicity as Glycopyrrolate, but exhibits an equal or higher anti-ulcer activity and further about 1/10 degree of corediatasis as side effect. This fact indicates that the Compound A is very useful as anticholinergic agent in comparison with known compounds which are now commercially available. Similar activities are also expected in other compounds of the present invention having the formula (I).

The present invention is further illustrated in greater detail by the following Reference Examples and Examples, but these Examples are given for illustrated purpose only and are not to be construed as limiting the scope of the present invention. Unless otherwise indicated, all parts, percents, ratios and the like are by weight.

REFERENCE EXAMPLE 1

(a) A mixture of 32 g of o-aminothiophenol and 62 g of ethyl benzalmalonate was heated at 90° C. for 5 hours and then allowed to stand to crystallize. The resulting crystals were then recrystallized from diethyl ether-petroleum ether to obtain 90 g of diethyl 2-(o-aminophenylthio)-2-phenylethane-11-dicarboxylate as colorless needles having a melting point of 71° C.

Elementary Analysis: Calc'd for $C_{20}H_{23}NO_4S$ (M.W. 373.475): C, 64.32; H, 6.21; N, 3.75 (%); Found: C, 64.25; H, 6.26; N, 3.72 (%)

(b) 74.6 g of the product obtained in (a) above was mixed with 1.4 g of triethylamine hydrochloride and the mixture was heated at about 180° C. until no further ethanol was distilled out (for about 2 hours). After allowing the reaction mixture to cool, a mixture of benzene-petroleum ether was added thereto and the mixture was then thoroughly stirred and filtered. The resulting filter cake was recrystallized from a mixture of chloroform-petroleum ether to obtain 35 g of 2,3-dihydro-3-ethoxycarbonyl-2-phenyl-1,5-benzothiazepin-4(5H)-one as colorless needles having a melting point of 199° C.

Elementary Analysis: Calc'd for $C_{18}H_{17}NO_3S$ (M.W. 327.405): C, 66.04; H, 5.23; N, 4.28 (%); Found: C, 66.17; H, 5.29; N, 4.21 (%)

(c) 32.7 g of the product obtained in (b) above was added in small portions to a mixture of 150 ml of tetrahydrofuran and 35 g of lithium aluminum hydride with stirring, followed by heating under refluxing for 3 hours. After cooling, methanol was added to the reaction mixture to decompose any excess of the remaining lithium aluminum hydride. The resulting solution was poured into ice water which had been rendered acidic with hydrochloric acid, and the precipitated crystals were filtered and recrystallized from a mixture of dimethylformamide-water to obtain 23.2 g of 2,3-dihydro-3-hydroxymethyl-2-phenyl-1,5-benzothiazepin-4(5H)-one having a melting point of 248° C.

Elementary Analysis: Calc'd for $C_{16}H_{15}NO_2S$ (M.W. 285.367) C, 67.34; H, 5.30; N, 4.91 (%); Found: C, 67.30; H, 5.24; N, 4.82 (%)

REFERENCE EXAMPLE 2

(a) A mixture of 32 g of o-aminothiophenol, 70.7 g of p-chlorobenzalmalonate and 1.4 g of pyridine hydrochloride was heated at about 180° C. until no further ethanol was distilled out (for about 4 hours). After allowing the reaction mixture to cool, a mixture of benzene-petroleum ether was added to the reaction mixture which was then thoroughly stirred and filtered. The resulting filter cake was recrystallized from chloroform-petroleum ether to obtain 54.5 g of 2-(p-chlorophenyl)-2,3-dihydro-3-ethoxycarbonyl-1,5-benzothiazepin-4(5H)-one as colorless needles having a melting point of 206° C.

Elementary Analysis: Calc'd for $C_{18}H_{16}ClNO_3S$: (M.W. 361.850): C, 59.75; H, 4.46; N, 3.87 (%); Found: C, 59.83; H, 4.40; N, 3.84 (%)

(b) 36.2 g of the product obtained in (a) above was added in small portions to a mixture of 100 ml of dioxane and 2.5 g of lithium aluminum hydride with stirring, followed by heating at 80° C. for 3 hours. After cooling, methanol was added to the reaction mixture to decompose any excess of the remaining lithium aluminum hydride. The resulting solution was poured into ice water which had been rendered acidic with hydrochloric acid, and the precipitated crystals were filtered and recrystallized from dimethylformamide-water to obtain 19.8 g of 2-(p-chlorophenyl)-2,3-dihydro-3-hydroxymethyl-1,5-benzothiazepin-4(5H)-one as colorless prisms having a melting point of 23.9° C.

Elementary Analysis: Calc'd for $C_{16}H_{14}ClNO_2S$ (M.W. 319.812) C, 60.09; H, 4.41; N, 4.38 (%); Found: C, 60.16; H, 4.37; N, 4.45 (%)

REFERENCE EXAMPLE 3

(a) A mixture of 32 g of o-aminothiophenol, 65.6 g of p-methylbenzalmalonate and 1.4 g of triethylamine hydrochloride was heated at about 180° C. until no further ethanol was distilled out (for about 3 hours). The resulting reaction mixture was worked up in the same manner as described in Reference Example 2 (a) and the crystals thus obtained was recrystallized from chloroform-petroleum ether to obtain 34 g of 2,3-dihydro-3-ethoxycarbonyl-2-(p-tolyl)-1,5-benzothiazepin-4(5H)-one as light yellow needles having a melting point of 185° C.

Elementary Analysis: Calc'd for $C_{19}H_{19}NO_3S$ (M.W. 341.432) C, 66.84; H, 5.61; N, 4.10 (%); Found: C, 66.70; H, 5.53; N, 4.00 (%)

(b) 34 g of the product obtained in (a) above was added in small portions to a mixture of 200 ml of tetrahydrofuran and 3.5 g of lithium aluminum hydride with stirring, followed by heating under refluxing for 3 hours. The resulting reaction mixture was then worked up in the same manner as described in Reference Example 1 (c) and the crystals thus obtained were recrystallized from dimethylformamide-water to obtain 16.8 g of 2,3-dihydro-3-hydroxymethyl-2-(p-tolyl)-1,5-benzothiazepin-4(5H)-one as colorless prisms having a melting point of 229° C.

Elementary Analysis: Calc'd for $C_{17}H_{17}NO_2S$ (M.W. 299.395) C, 68.20; H, 5.72; N, 4.68 (%); Found: C, 68.12; H, 5.78; N, 4.53 (%)

REFERENCE EXAMPLE 4

(a) A mixture of 32 g of o-aminothiophenol, 69.6 g of ethyl p-methoxybenzalmalonate and 1.6 g of triethylamine hydrochloride was heated at about 180° C. until no further ethanol was distilled out (for about 4 hours). The resulting mixture was then worked up in the same manner as described in Reference Example 2 (a) and the crystals thus obtained were recrystallized from chloroform-petroleum ether to obtain 25 g of 2,3-dihydro-3-ethoxycarbonyl-2-(p-methoxyphenyl)-1,5-benzothiazepin-4(5H)-one as colorless needles having a melting point of 192° C.

Elementary Analysis: Calc'd for $C_{19}H_{19}NO_4S$ (M.W. 357.432) C, 63.85; H, 5.36; N, 3.92 (%); Found: C, 63.69; H, 5.42; N, 3.86 (%)

(b) 18 g of the product obtained in (a) above was added in small portions to a mixture of 70 ml of tetrahydrofuran and 1.3 g of lithium aluminum hydride with stirring, followed by heating under refluxing for 3 hours. The resulting reaction mixture was then worked up in the same manner as described in Reference Example 1 (c) to obtain 9.8 g of 2,3-dihydro-3-hydroxymethyl-2-(p-methoxyphenyl)-1,5-benzothiazepin-4(5H)-one as colorless needles having a melting point of 217° C.

Elementary Analysis: Calc'd for $C_{17}H_{17}NO_3S$ (M.W. 315.394) C, 64.74; H, 5.43; N, 4.44 (%); Found: C, 64.63; H, 5.40; N, 4.47 (%)

EXAMPLE 1

(a) 5.7 g of 2,3-dihydro-3-hydroxymethyl-2-phenyl-1,5-benzothiazepin-4(5H)-one prepared as described in Reference Example 1 and 1.6 g of pyridine were dissolved in 30 ml of benzene, and 3.6 g of thionyl chloride was added to the solution, followed by heating under refluxing for 1 hour. The solvent was then distilled off and water was added to the residue. The precipitated crystals were filtered, washed with methanol and recrystallized from benzene to obtain 5.1 g of 3-chloromethyl-2,3-dihydro-2-phenyl-1,5-benzothiazepin-4(5H)-one as colorless needles having a melting point of 233° C. (with decomposition).

Elementary Analysis: Calc'd for $C_{16}H_{14}ClNOS$ (M.W. 303.813): C, 63.26; H, 4.64; N, 4.61 (%); Found: C, 63.35; H, 4.60; N, 4.53 (%)

(b) 4.5 g of the product obtained in (a) above was added to 10 ml of N-methylpiperazine with stirring, and the mixture was heated under refluxing for 2 hours. After allowing the mixture to cool, water was added to the mixture and the precipitated crystals were separated by filtration. The filter cake was added to 20 ml of methanol and the solution was heated and then cooled. The methanol-insoluble substance (a product in a trans form) was separated by filtration and set aside. The filtrate was concentrated and the resulting residue was recrystallized from a mixture of benzene-diethyl ether to obtain cis-2,3-dihydro-3-[(4-methylpiperazinyl)methyl]-2-phenyl-1,5-benzothiazepin-4(5H)-one as colorless prisms having a melting point of 198° C.

Elementary Analysis: Calc'd for $C_{21}H_{25}N_3OS$ (M.W. 367.517): C, 68.63; H, 6.86; N, 11.43 (%); Found: C, 68.52; H, 6.85; N, 11.39 (%)

EXAMPLE 2

(a) 3 g of 2,3-dihydro-3-hydroxymethyl-2-(p-tolyl)-1,5-benzothiazepin-4(5H)-one prepared as described in Reference Example 3 was dissolved in 15 ml of pyridine. 1.3 g of methanesulfonyl chloride was added to the solution and the mixture was stirred at room temperature for 2 hours. Water was added to the reaction mixture and the precipitated crystals were separated by filtration and recrystallized from dichloromethane-n-hexane to obtain 3.3 g of 2,3-dihydro-3-[(methylsulfonyloxy)methyl]-2-(p-tolyl)-1,5-benzothiazepin-4(5H)-one as colorless needles having a melting point of 207° C.

Elementary Analysis: Calc'd for $C_{18}H_{19}NO_4S_2$ (M.W. 377.484): C, 57.27; H, 5.07; N, 3.71 (%); Found: C, 57.42; H, 5.14; N, 3.58 (%)

(b) 1.8 g of the product obtained in (a) above was added to 6 ml of N-methylpiperazine and the mixture was heated at 90° C. for 30 minutes while stirring. After allowing the mixture to cool, water was added to the mixture and the precipitated crystals were separated by filtration. The filter cake was extracted with dichloromethane and most of the solvent was distilled off and diethyl ether was added to the residue. The mixture was allowed to stand and the precipitated crystals (a product in a trans form) was separated by filtration. The filtrate was concentrated under reduced pressure and the resulting residue was recrystallized from benzene-diethyl ether to obtain cis-2,3-dihydro-3-[(4-methylpiperazinyl)methyl]-2-(p-tolyl)-1,5-benzothiazepin-4(5H)-one as colorless prisms having a melting point of 196° C.

Elementary Analysis: Calc'd for $C_{22}H_{27}N_3OS$ (M.W. 381.544): C, 69.26; H, 7.13; N, 11.01 (%); Found: C, 69.45; H, 7.18; N, 10.88 (%)

EXAMPLE 3

(a) 5.7 g of 2,3-dihydro-3-hydroxymethyl-2-phenyl-1,5-benzothiazepin-4(5H)-one prepared as described in Reference Example 1 was dissolved in 20 ml of triethylamine. 3.8 g of p-toluenesulfonyl chloride was added to the solution while stirring and the mixture was stirred at room temperature for 2 hours. Water was added to the reaction mixture and the precipitated crystals were separated by filtration and recrystallized from a mixture of dichloromethane-n-hexane to obtain 8 g of 2,3-dihydro-2-phenyl-3-[(p-toluenesulfonyloxy)methyl]-1,5-benzothiazepin-4(5H)-one as colorless prisms having a melting point of 215° C.

Elementary Analysis: Calc'd for $C_{23}H_{21}NO_4S_2$ (M.W. 439.556): C, 62.85; H, 4.82; N, 3.19 (%); Found: C, 62.74; H, 4.78; N, 3.10 (%)

(b) 2.2 g of the product obtained in (a) above was added to 6 ml of piperazinoethanol and the mixture was heated at 100° C. for 5 hours. After allowing the mixture to cool, water was added to the mixture and the precipitated crystals were separated by filtration. 10 ml of methanol was added to the crystals thus obtained and the mixture was heated for 30 minutes under refluxing.

After allowing the mixture to cool, the insoluble substance (a product in a trans form) was separated by filtration and the filtrate was concentrated under reduced pressure. The resulting residue was recrystallized from a mixture of benzenediethyl ether to obtain cis-2,3-dihydro-4-[(4-hydroxyethylpiperazinyl)methyl]-2-phenyl-1,5-benzothiazepin-4(5H)-one as colorless prisms having a melting point of 106° C.

Elementary Analysis: Calc'd for $C_{22}H_{27}N_3O_2S$ (M.W. 397.543): C, 66.47; H, 6.85; N, 10.57 (%); Found: C, 66.59; H, 6.90; N, 10.57 (%)

dro-3-[(4-methylpiperazinyl)methyl]-2-phenyl-1,5-benzothiazepin-4(5H)-one dihydrochloride monohydrate as colorless needles having a melting point of 212° C. (with decomposition).

Elementary Analysis: Calc'd for $C_{21}H_{25}N_3OS.2HCl.H_2O$ (M.W. 458.454): C, 55.02; H, 6.38; N, 9.17 (%); Found: C, 55.20; H, 6.52; N, 9.10 (%)

EXAMPLES 5-14

According to the procedures as described in Examples 1 to 4, the following 1,5-benzothiazepine compounds and the salts thereof were prepared.

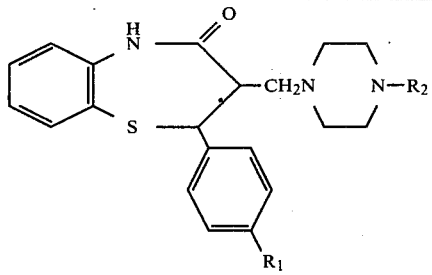

| Example No. | Cis or Trans | $R_1$ | $R_2$ | Salt | Recrystallization Solvent and Crystal Form | Melting Point (°C.) | Empirical Formula (Molecular Weight) | Elementary Analysis Values Found (Calculated Values in Parentheses) | | |
|---|---|---|---|---|---|---|---|---|---|---|
| | | | | | | | | C | H | N |
| 5 | Cis | —H | —CH$_3$ | Dimaleate | Ethanol, Colorless Needles | 165° C. (with decomp.) | $C_{21}H_{25}N_3OS$ . $2C_4H_4O_4$ (599.665) | 58.26 (58.09) | 5.51 5.55 | 6.84 7.01 |
| 6 | Cis | —H | —CH$_3$ | Methyl Bromide, Monohydrate | Acetone Methanol, Colorless Prisms | 271° C. (with decomp.) | $C_{22}H_{28}BrN_3OS$ . $H_2O$ (480.476) | 54.86 (55.00) | 6.25 6.29 | 8.72 8.75) |
| 7 | Trans | —H | —CH$_3$ | Dimaleate | Ethanol, Colorless Needles | 175° C. (with decomp.) | $C_{21}H_{25}N_3OS$ . $2C_4H_4O_4$ (599.665) | 58.07 (58.09) | 5.43 5.55 | 6.85 7.01) |
| 8 | Cis | —CH$_3$ | —CH$_3$ | Dihydrochloride Monohydrate | Aqueous Methanol, Colorless Needles | 228° C. (with decomp.) | $C_{22}H_{27}N_3OS$ . $2HCl . H_2O$ (472.481) | 55.98 (55.93) | 6.57 6.61 | 8.74 8.89) |
| 9 | Cis | —H | —H | Free | Benzene | 188° C. | $C_{20}C_{23}N_3OS$ | 68.12 (67.96) | 6.47 6.56 | 11.85 11.89) |
| 10 | Cis | —H | —CH$_2$CH$_2$OH | Dihydrochloride Monohydrate | Aqueous Methanol, Colorless Needles | 249° C. (with decomp.) | $C_{22}H_{27}N_3O_2S$ . $2HCl . H_2O$ (488.481) | 54.02 (54.10) | 6.43 6.40 | 8.56 8.60) |
| 11 | Cis | —Cl | —CH$_3$ | Free | Chloroform-Ethanol, Colorless Prisms | 248° C. (with decomp.) | $C_{21}H_{24}C N_3OS$ (401.962) | 62.79 (62.75) | 5.90 6.02 | 10.38 10.45) |
| 12 | Cis | —Cl | —CH$_3$ | Dihydrochloride Monohydrate | Aqueous Methanol, Colorless Needles | 237° C. (with decomp.) | $C_{21}H_{24}ClN_3OS$ . $2HCl . H_2O$ (492.899) | 51.28 (51.17) | 5.69 5.73 | 8.39 8.53) |
| 13 | Cis | —OCH$_3$ | —CH$_3$ | Free | Benzene-Diethyl Ether, Colorless Prisms | 193° C. | $C_{22}H_{27}N_3O_2S$ (397.543) | 66.41 (66.47) | 6.83 6.85 | 10.62 10.57) |
| 14 | Cis | —OCH$_3$ | —CH$_3$ | Dihydrochloride Monohydrate | Aqueous Methanol Colorless Prisms | 211° C. (with decomp.) | $C_{22}H_{27}N_3O_2S$ . $2HCl . H_2O$ (488.481) | 54.32 (54.10) | 6.32 6.40 | 8.49 8.60) |

EXAMPLE 4

(a) 3.6 g of cis-2,3-dihydro-3-[(4-methylpiperazinyl)methyl]-2-phenyl-1,5-benzothiazepin-4(5H)-one was dissolved in 10 ml of ethanol, and 2.5 ml of concentrated hydrochloric acid was added to the solution while stirring. The precipitated crystals were filtered and recrystallized from aqueous methanol to obtain cis-2,3-dihy-

EXAMPLES 15-17

According to the procedures as described in Examples 1 to 4, the following 1,5-benzothiazepine intermediates having the formula (II) or (III) were prepared.

15. 3-chloromethyl-2,3-dihydro-2-(p-methoxyphenyl)-1,5-benzothiazepin-4(5H)-one(II). Recrystallized from chloroform-n-hexane. Colorless needles having a melting point 235° C. (with decomposition).

Elementary Analysis: Calc'd for $C_{17}H_{16}ClNO_2S$ (M.W. 333,840): C, 61.16; H, 4.83; N, 4.20(%); Found: C, 61.10; H, 4.88; N, 4.04(%)

16. 3-chloromethyl-2-(p-chlorophenyl)-2,3-dihydro-1,5-benzothiazepin-4(5H)-one(II). Recrystallized from chloroform-n-hexane. Colorless prisms having a melting point of 241° C. (with decomposition).

Elementary Analysis: Calc'd. for $C_{16}H_{13}Cl_2NOS$ (M.W. 338,258): C, 56.81; H, 3.87; N, 4.14(%); Found: C, 56.93; H, 3.81; N, 4.12(%)

17. 2,3-dihydro-3-methylsulfonyloxymethyl-2-phenyl-1,5-benzothiazepin-4(5H)-one(III). Recrystallized from dichloromethane-n-hexane. Colorless needles having a melting point of 215° C.

Elementary Analysis: Calc'd. for $C_{17}H_{17}NO_4S_2$ (M.W. 363,457) C, 56.18; H, 4.71; N, 3.85(%); Found: C, 56.05; H, 4.78; N, 3.82(%)

EXAMPLE 18

To a solution of 20 g of cis-(±)-2,3-dihydro-3-[(4-methyl piperazinyl)methyl]-2-phenyl-1,5-benzothiazepin-4(5H)-one dissolved in 200 ml of methanol was added a solution of 10 g of (+)-tartaric acid dissolved in 50 ml of methanol, and the mixture was allowed to stand overnight at room temperature. The precipitated crystals were separated by filtration and recrystallized from aqueous methanol to obtain 8.7 g of a (+)-tartarate of the compound in the (+) form as colorless flake-like crystals having a melting point of 192° C.

The resulting tartarate was dissolved in 200 ml of water and the solution was rendered neutral with potassium carbonate. The precipitated crystals were separated by filtration, washed with water and recrystallized from dichloromethane-petroleum ether to obtain 5.8 g of cis-(+)-2,3-dihydro-3-[(4-methylpiperazinyl)methyl]-2-phenyl-1,5-benzothiazepin-4(5H)-one as colorless prisms having a melting point of 198° C. $[\alpha]_D^{20} = +46°$ (c=2.4, chloroform)

Elementary Analysis: Calc'd for $C_{21}H_{25}N_3OS$ (M.W. 367,517): C, 68.63; H, 6.86; N, 11.43(%); Found: C, 68.58; H, 6.92; N, 11.40(%)

The filtrate which had been set aside when the above crude (+) tartarate of (+) compound was filtered was concentrated under reduced pressure. The resulting oily substance was dissolved in 200 ml of water and the solution was rendered neutral with potassium carbonate. The precipitated crystals were separated by filtration and dissolved in 100 ml of methanol. To the resulting solution was then added a solution of 4.5 g of (−)-tartaric acid dissolved in 30 ml of methanol, and the mixture was allowed to stand overnight at room temperature. The precipitated crystals were filtered and recrystallized from aqueous methanol to obtain 7.5 g of a (−)-tartarate of the compound in the (−) form as colorless needles having a melting point of 193° C.

The resulting tartarate was dissolved in 200 ml of water and the solution was rendered neutral with potassium carbonate. The precipitated crystals were separated by filtration and recrystallized from dichloromethane-petroleum ether to obtain 5.2 g of cis-(−)-2,3-dihydro-3-[(4-methylpiperazinyl)methyl]-2-phenyl-1,5-benzothiazepin-4(5H)-one as colorless prisms having a melting point of 198° C. $[\alpha]_D^{20} = -46°$ (c=2.4, chloroform)

Elementary Analysis: Calc'd for $C_{21}H_{25}N_3OS$ (M.W. 367,517): C, 68.63; H, 6.86; N, 11.43(%); Found: C, 68.75; H, 6.95; N, 11.31(%)

EXAMPLE 19

20 g of cis-(±)-2,3-dihydro-3-[(4-methylpiperazinyl)methyl]-2-phenyl-1,5-benzothiazepin-4(5H)-one was dissolved in 400 ml of a mixture of methanol-ethanol (50:50 by volume). To the resulting solution was added a solution of 8.2 g of (−)-tartaric acid dissolved in 100 ml of a mixture of methanol-ethanol (50:50 by volume) and the resulting mixture was allowed to stand overnight at room temperature. The precipitated crystals were separated by filtration and recrystallized from aqueous methanol to obtain 9 g of a (−)-tertarate of the (−) form compound as colorless needles having a melting point of 193° C. The crystals thus obtained were dissolved in 200 ml of water and the solution was rendered neutral with sodium carbonate. The precipitated crystals were then separated by filtration, washed with water and recrystallized from dichloromethane-petroleum ether to obtain 5.8 g of cis-(−)-2,3-dihydro-3-[(4-methylpiperazinyl)methyl]-2-phenyl-1,5-benzothiazepin-4(5H)-one as colorless prisms having a melting point of 198° C. $[\alpha]_D^{20} = -46°$ (c=0.4, chloroform)

Elementary Analysis: Calc'd. for $C_{21}H_{25}N_3OS$ (M.W. 367,517) C, 68.63; H, 6.86; N, 11.43; Found: C, 68.70; H, 6.82; N, 11.45

EXAMPLE 20

5.2 g of cis-(−)-2,3-dihydro-3-[(4-methylpiperazinyl)methyl]-2-phenyl-1,5-benzothiazepine prepared as described in Example 18 or 19 was dissolved in 15 ml of ethanol and 3.6 ml of concentrated hydrochloric acid was added to the solution with stirring. The precipitated crystals were separated by filtration and recrystallized from aqueous methanol to obtain cis-(−)-2,3-dihydro-3-[(4-methylpiperazinyl)methyl]-2-phenyl-1,5-benzothiazepin-4(5H)-one dihydrochloride as colorless needles having a melting point of 231° C. (with decomposition). $[\alpha]_D^{20} = -56°$ (c=0.4, water).

Elementary Analysis: Calc'd for $C_{21}H_{25}N_3OS \cdot 2HCl$ (M.W. 440,439): C, 57.27; H, 6.18; N, 9.54(%); Found: C, 57.40; H, 6.22; N, 9.46(%)

EXAMPLE 21

7 g of cis-(−)-2,3-dihydro-3-[(4-methylpiperazinyl)methyl]-2-phenyl-1,5-benzothiazepin-4(5H)-one was dissolved in 100 ml of dichloromethane and the resulting solution was added to 30 ml of a methanolic solution of 5 g of methyl bromide. The mixture was then allowed to stand for 10 hours at room temperature and the solvent was distilled out. Dichloromethane and diethyl ether were added to the residue and the precipitated crystals were separated by filtration and recrystallized from ethanol to obtain cis-(−)-2,3-dihydro-3-[(4-methylpiperazinyl)methyl]-2-phenyl-1,5-benzothiazepin-4(5H)-one di(methyl bromide)monohydrate as a white crystalline powder having a melting point of 259° C. (with decomposition). $[\alpha]_D^{20} = -53°$ (c=0.4, water)

Elementary Analysis: Calc'd. for $C_{23}H_{31}Br_2N_3OS \cdot H_2O$ (M.W. 575,410): C, 48.01; H, 5.78; N, 7.30(%); Found: C, 48.07; H, 5.69; N, 7.49(%)

EXAMPLES 22 TO 26

The following optically active 1,5-benzothiazepine compounds and salts thereof were prepared according to the procedure as described in Example 18 to 21.

22. Cis-(—)-2,3-dihydro-3-[(4-methylpiperazinyl)methyl]-2-phenyl-1,5-binzothiazepin-4(5H)-one dimaleate. Recrystallized from methanol-diethyl ether. White crystalline powder having a melting point of 190° C. (with decomposition). $[\alpha]_D^{20} = -52°$ (c=0.4, water)

Elementary Analysis: Calc'd for $C_{21}H_{25}N_3OS.2C_4H_4O_4$ (M.W. 599,665): C, 58.09; H, 5.55; N, 7.01(%); Found: C, 57.74; H, 5.65; N, 6.72(%)

23. Cis-(—)-2,3-dihydro-3-[(4-methylpiperazinyl)methyl]-2-phenyl-1,5-benzothiazepin-4(5H)-one di(methyl sulfate). Recrystallized from ethanol-diethyl ether. White crystalline powder having a melting point of 287° C. (with decomposition). $[\alpha]_D^{20} = -55°$ (c=0.4, water)

Elementary Analysis: Calc'd for $C_{23}H_{31}N_3O_5S_2$ (M.W. 493,649): C, 55.96; H, 6.33; N, 8.51(%); Found: C, 56.06; H, 6.39; N, 8.52(%)

24. Cis-(—)-2,3-dihydro-3-[(4-methylpiperazinyl)methyl]-2-phenyl-1,5-benzothiazepin-4(5H)-one di(methanesulfonate). Recrystallized from ethanol. White crystalline powder having a melting point of 256° C. (with decomposition). $[\alpha]_D^{20} = -47°$ (c=0.4, water)

Elementary Analysis: Calc'd for $C_{23}H_{33}N_3O_7S_3$ (M.W. 559,727): C, 49.36; H, 5.94; N, 7.51(%); Found: C, 49.23; H, 5.98; N, 7.46(%)

25. Cis-(—)-2,3-dihydro-3-[(4-methylpiperazinyl)methyl]-2-phenyl-1,5-benzothiazepin-4(5H)-one butyl bromide monohydrate. Recrystallized from acetone-diethyl ether. White crystalline powder having a melting point of 254° C. (with decomposition). $[\alpha]_D^{20} = -55°$ (c=0.4, water)

Elementary Analysis: Calc'd for $C_{25}H_{34}BrN_3OS.H_2O$ (M.W. 522,558): C, 57.46; H, 6.94; N, 8.04(%); Found: C, 57.55; H, 6.91; N, 8.11 (%)

26. Cis-(+)-2,3-dihydro-3-[(4-methylpiperazinyl)methyl]-2-phenyl-1,5-benzothiazepin-4(5H)-one dihydrochloride. Recrystallized from aqueous methanol. Colorless needles having a melting point of 231° C. (with decomposition). $[\alpha]_D^{20} = +55°$ (c=0.4, water)

Elementary Analysis: Calc'd for $C_{21}H_{25}N_3OS.2HCl$ (M.W. 440,439) C, 57.27; H, 6.18; N, 9.54(%) Found: C, 57.33; H, 6.17; N, 9.49(%)

What is claimed is:

1. A cis or trans-1,5-benzothiazepine compound represented by the formula (I)

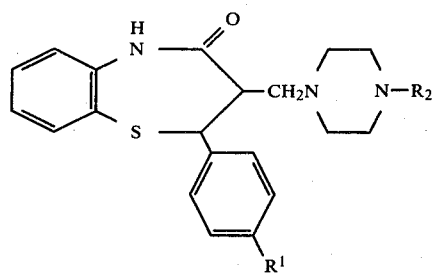

(I)

wherein $R_1$ represents a hydrogen atom, a halogen atom, a straight-chain or branched-chain alkyl group having 1 to 4 carbon atoms or a straight-chain or branched-chain alkoxy group having 1 to 4 carbon atoms and $R_2$ represents a hydrogen atom, a straight-chain or branched-chain alkyl group having 1 to 4 carbon atoms or a hydroxyalkyl group having 2 to 4 carbon atoms in which the alkyl moiety thereof may be straight-chain or branched-chain and the pharmaceutically acceptable acid addition salt and quaternary ammonium salt thereof.

2. The cis or trans-1,5-benzothiazepine compound according to claim 1 represented by the formula (I)

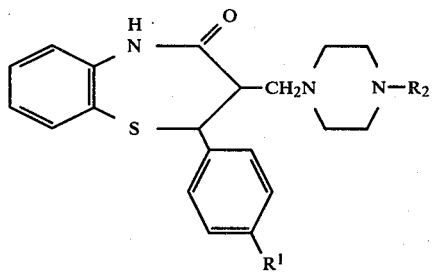

(I)

wherein $R_1$ represents a hydrogen atom, a chlorine atom, a methyl group or a methoxy group and $R_2$ represents a methyl group or a hydroxyethyl group, and the pharmaceutically acceptable acid addition salt and quaternary ammonium salt thereof.

3. (±)-Cis-2,3-dihydro-3-[(4-methylpiperazinyl)methyl]-2-phenyl-1,5-benzothiazepin-4(5H)-one according to claim 1 represented by the formula (I)

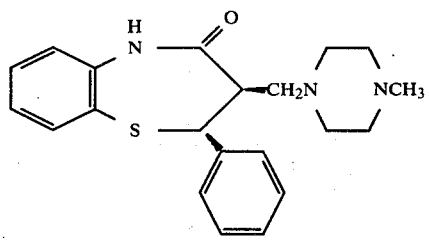

and the pharmaceutically acceptable acid addition salt and quaternary ammonium salt thereof.

4. (—)-Cis-2,3-dihydro-3-[(4-methylpiperazinyl)methyl]-2-phenyl-1,5-benzothiazepin-4(5H)-one and the pharmaceutically acceptable acid addition salt and quaternary ammonium salt thereof.

* * * * *